United States Patent [19]

Necker et al.

[11] 4,037,462
[45] July 26, 1977

[54] METHOD OF AND ASSEMBLY FOR MONITORING THE DRY DENSITY OF A BOARD PRODUCT

[75] Inventors: Carl George Necker, Littleton; Richard Rial Colwell, Englewood, both of Colo.

[73] Assignee: Johns-Manville Corporation, Denver, Colo.

[21] Appl. No.: 731,381

[22] Filed: Oct. 12, 1976

[51] Int. Cl.[2] ............................................. G01N 9/00
[52] U.S. Cl. ...................................... 73/32 R; 73/433
[58] Field of Search ............... 73/32 R, 433, 435, 436, 73/61.1 R

[56] References Cited

U.S. PATENT DOCUMENTS 3,436,968  4/1969  Unger et al. .......................... 73/433

FOREIGN PATENT DOCUMENTS 1,238,028  6/1960  France ................................... 73/433

*Primary Examiner*—James J. Gill
*Attorney, Agent, or Firm*—Robert M. Krone; Joseph J. Kelly; Stephen C. Shear

[57] ABSTRACT

As disclosed herein, the dry density of a board product is monitored, preferably continuously so. The board is made by a wet forming process, which process includes preparing an aqueous slurry of at least some of the board's components, depositing the slurry upon a moving screen to form a moisture-laden sheet thereon, and removing the moisture to form the ultimate product. The dry density of this product is monitored by first simultaneously and automatically measuring the wet weight, moisture content and thickness of the water-laden sheet on the moving screen and from these measurements automatically calculating the dry density of the board product to be produced from the measured sheet.

6 Claims, 1 Drawing Figure

METHOD OF AND ASSEMBLY FOR MONITORING THE DRY DENSITY OF A BOARD PRODUCT

BACKGROUND OF THE INVENTION

The present invention relates generally to monitoring the dry density of a board product made by a wet forming process and more particularly to monitoring its dry density in-line, that is, without removing a sample, and preferably continuously throughout the manufacture of the board product.

One common way in which board products such as perlite insulation board or mineral wool acoustical board are made is by a wet forming process. In accordance with this process, a dilute aqueous slurry comprising at least some of the ingredients or components of the product is prepared. This slurry is deposited on a moving screen, either a generally horizontal screen comprising part of a Fourdrinier type machine or a cylindrical screen comprising part of an Oliver machine, to form a moisture-laden sheet thereon. This moisture-laden sheet moves between a number of press rolls and ultimately into a dryer where its moisture is removed so as to form the final board product.

It should be obvious that there are a number of physical characteristics which affect the ultimately formed board, from not only a performance standpoint but also from a cost standpoint. For example, if the ultimate product is formed thicker than the specifications require, the product may be more expensive than need be, whereas if the ultimate product is too thin its performance may be seriously compromised. In a similar fashion, it may be quite costly to make a product which is more dense than required, and where insulation values or acoustical values are critical an overly dense product may seriously compromise these values. Still another factor to be considered and one which will not necessarily affect the ultimate product but rather its process of manufacture is the moisture content in the moisture-laden sheet. It can be quite costly from an energy usage standpoint to include more moisture in the sheet than is necessary. By the same token, where the sheet is not formed with sufficient moisture the ultimate physical characteristics of the end product could be adversely affected.

From the foregoing, the importance of monitoring the dry density and thickness of a board product of the type to which the present invention is directed and the monitoring of its moisture content when still in a moisture-laden state should be quite clear. However, Applicants have found that the data obtained for a given sample in this monitoring procedure, for most efficient use of the procedure, must be obtained as soon as possible after initial formation of the sample. More specifically, when this data is obtained a prolonged period after formation of the sample, the data is not nearly as helpful in making adjustments to the overall process as would be the case if the data were obtained immediately after formation of the sample. And yet, to Applicants' knowledge, the typical monitoring system being used today requires a substantial time lag between formation of a given sample and obtaining data relating to its dry density.

In accordance with this typical monitoring procedure, the moisture-laden sheet on the moving screen is monitored for wet weight and thickness, this being accomplished continuously and in-line throughout the manufacturing process. However, its moisture content is not obtained in this way and hence neither is its ultimate dry density. Rather, to obtain moisture content, a given sample is actually removed from the line, weighed, and placed in an oven to dry. It is then weighed again and from this dry weight along with the wet weight and thickness of the sample the dry density of the sample is calculated. However, this drying procedure takes at least 20 minutes (generally longer) and hence by the time the data is obtained the process may be running entirely different than at the time the sample was measured. This of course makes it difficult if not completely unreliable to make adjustments in the process based on the dry density obtained. Specifically, the operator is never certain that the hand samples made at least 20 minutes earlier are representative of the wet weight, thickness and moisture content of the moisture-laden sheet presently being formed on the moving wire or that it is representative of the dry density of the product being formed from the present moisture-laden sheet. Hence, it is difficult, if not impossible, for the operator to accurately and reliably make the appropriate changes to the process where necessary.

As will be seen hereinafter, the monitoring procedure of the present invention eliminates the long time delay between formation of the sample to be monitored and the actual monitoring thereof. In this way, any corrections in the overall process to compensate for undesirable physical characteristics can be made immediately. Moreover, by monitoring any given sample and obtaining data on that sample immediately after it is formed and preferably by doing this continuously in-line the operator obtains immediate feedback as to the success of his process adjustments and hence can quickly learn what process manipulations are required to continuously maintain the ultimate product within specification.

SUMMARY OF THE INVENTION

As stated previously, the present invention is directed to both a method of and assembly for monitoring the dry density of a board product, for example a perlite insulation board or a mineral wool acoustical board, made by a wet forming process. This process, which may be for example a Fourdrinier type process or an Oliver (cylinder) type process, calls for the preparation of an aqueous slurry of at least some of the components making up the product. The slurry is deposited on a moving screen to form a moisture-laden sheet thereon and the moisture is removed from this sheet to form the end product. In accordance with the present invention, the wet weight, moisture content and thickness of the water-laden sheet are measured as the sheet moves on the screen, i.e., in-line. From these in-line measurements the dry density of the board product to be produced from the measured sheet is automatically calculated.

In a preferred embodiment of the present invention, the wet weight, moisture content and thickness of the moisture-laden sheet are continuously measured during the manufacture of the board product and these measurements and the dry density are continuously visually displayed by representative curves. By providing this continuous procedure with a visual output the operator can quickly compensate for errors in the process and can immediately receive feedback based on what corrections he has made so as to make further corrections if necesary or merely to know that furthr corrections are not necessary.

BRIEF DESCRIPTION OF THE DRAWING

Sole

DETAILED DESCRIPTION AND PREFERRED EMBODIMENT

Figure 1:
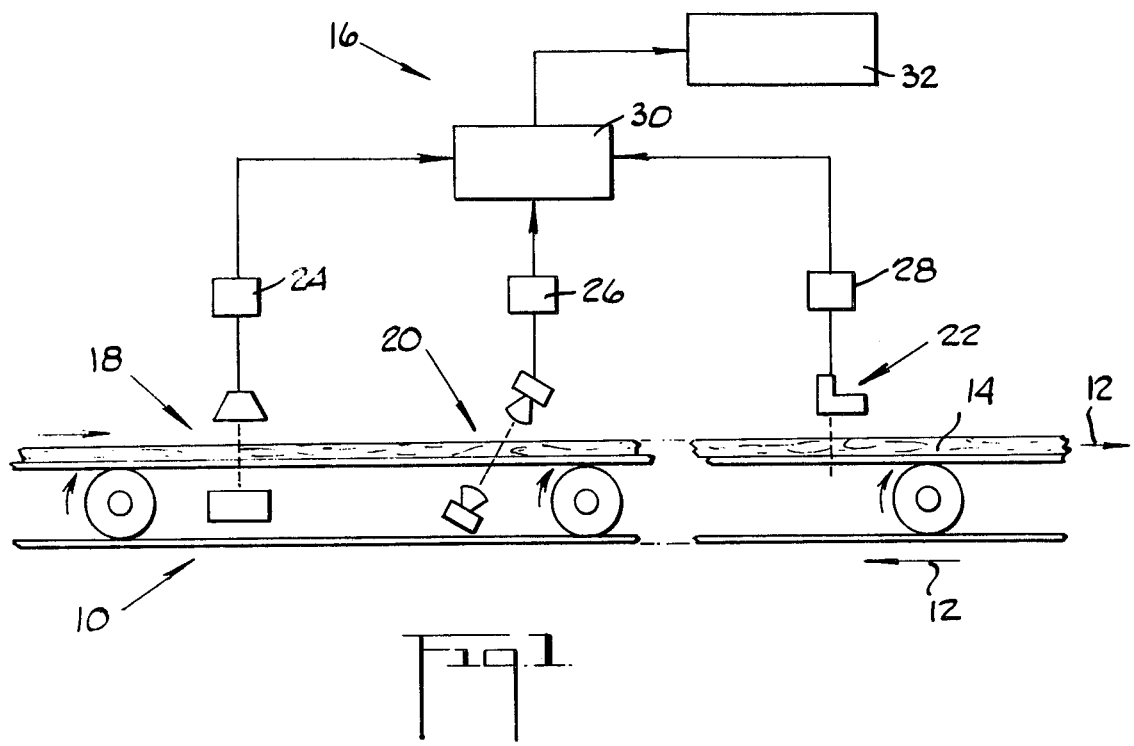
FIG. 1 is, in part, a side elevational view of a portion of a wet forming machine for making board product and in part a block diagram of an assembly for monitoring the dry density of the board product made by this machine.

Turning to sole FIG. 1, a conveyor system 10 moving in the direction of arrows 12 is illustrated. This conveyor system is part of an overall apparatus for manufacturing a board product, for example a perlite insulation board or mineral wool acoustical board, by means of a wet forming process. This process may be of conventional type well known to those skilled in the art and hence will not be discussed in detail herein. Briefly, however, it should be pointed out that this process requires the preparation of a dilute aqueous slurry of at least some of the components or ingredients making up the product. For example where the product is a perlite insulation board, the slurry will include a known percentage of expanded perlite particles, a known percentage of fiber, for example newsprint, and a known percent of asphalt emulsion and quite possibly other ingredients. where the board product is to be a mineral wool insulation board, the slurry will include mineral wool fiber, newsprint fiber, starch and clay, all in specific known amounts. The slurry, which is held in a large vat or headbox, is deposited on a moving screen where by means of suction a moisture-laden sheet is formed. Where the overall apparatus is a conventional Fourdrinier type machine the moving screen or wire as it is commonly called will be generally horizontal, actually at a slight incline, and moves in a straight-line path. Where the apparatus is an Oliver machine, commonly referred to as a cylinder machine, the moving screen will be cylindrical and its movement will be one of rotation rather than straight-line movement. The moisture-laden sheet, once formed, moves through a series of press rolls and conventional vacuum stations where it is compressed to the desired thickness and where as much as water as possible is extracted. Inasmuch as not all of the water can be removed in this way, the moisure-laden sheet eventually moves into a dryer where it is completely dried so as to form the end product.

In FIG. 1 the moisture-laden sheet, generally designated at 14, is shown at a point just downstream from the press section (not shown) of the overall apparatus, that is, just after it has passed through the press rolls and vacuum stations and just before entering th dryer. It is at this point that an assembly, generally designated at 16, is provided for monitoring the sheet in a way to be described in detail below.

As illustrated in FIG. 1, monitoring assembly 16 includes arrangements 18, 20 and 22 which are provided for measuring different characteristics of moisture-laden sheet 14 so as to ultimately calculate the dry density of the board product to be produced from the measured sheet. Arrangement 18 measures the wet weight (commonly referred to as the mass) of the moisture-laden sheet at the point of measurement. Arrangement 20 measures the moisture content of the sheet. Arrangement 22 measures its thickness. All of these measurements are carried out without removing a sample from the conveyor system, in other words they are carried out in-line, and preferably continuously throughout the manufacture of the board product.

Each of these arrangements is or may be conventional, using conventional componenets readily selected and combined by those skilled in the art. In an actual working embodiment, arrangement 18 for measuring the wet weight of moisture-laden sheet 14 is actually a nuclear gauge. Arrangement 20 for detecting the moisture content of sheet 14 is actually a microwave absorption gauge manufactured by Acurex Corporation under the trade name ACUREX and thickness measuring arrangement 22 is actually a caliper detector which measures thickness by means of capacitance. It should be noted that each arrangement produces an electrical output signal which corresponds to the characteristics being measured. Each representative signal is first conditioned, that is, converted from millivolts to volts, while of course retaining its representative characteristic, by conventional means designated at 24, 26 and 28 respectively. These conditioned signals are then applied to a conventional arrangement 30 which by calculation converts them to a signal representative of the dry density of the board product to be produced from the measured sheet.

As just stated, arrangement 30 receives at its input signals representative of the wet weight, moisture content and thickness of moisture-laden sheet 14 as the sheet passes from the press section of the overall wet forming mahine and just before it enters the dryer. Arrangement 30 by convenional electronics performs the following calculations:

1. wet weight (1bs/ft$^2$) − moisture content (1bs/ft$^2$) = dry weight (1bs/ft$^2$)
2. dry weight (1bs/ft$^2$) ÷ thickness (ft) = dry density (1bs/ft$^3$).

After performing the calculations just set forth, arrangement 30 produces an output signal representative of dry density and this signal is applied to the input of a conventional visual display readout 32, for example a curve drawing recorder. This readout is preferably a continuing curve located in a time vs magnitude coordinate system. In a preferred embodiment of the present invention, the outputs from arrangements 18, 20 and 22, that is, the signals representative of wet weight, moisture content and thickness are also applied directly to the readout so that these characteristics may also be visually displayed in and by themselves. These characteristics are also preferably indicated by the same type of time vs magnitude curve.

From the time a given amount of aqueous slurry is prepared to the time a moisture-laden sheet 14 made from that particular slurry reaches monitoring assembly 16, approximately 4 minutes elapse. Hence, should assembly 16 indicate that an adjustment is required, if the adjustment is made immediately the maximum time lag is only 4 minutes as opposed to for example the twenty minutes or more required in the previously described prior art monitoring approach. This rather short lag has a number of advantages, as discussed previously. Where corrections are made immediately, material waste can be reduced substantially. Moreover, in making these adjustments immediately, the operator immediately obtains a feedback on the effects from these adjustments. If further adjustments are necessary they can be carried out at that time and not after substantial delays.

Another advantage and one relating to this rather rapid feedback is that the operator can experiment on various adjustment approaches to the process for correcting problems in wet weight, moisture content, thickness and/or dry density itself. For example, it has been known that if the operator increases flow of water and solids to the moving wire (or cylinder) he will increasse thickness, moisture content and density, that is, in an absolute sense. By the same token, it has always been assumed that if one reduced the slurry flow to the wire (or cylinder) he would automatically reduce the thickness, moisture content and density in the ultimate product. However, based on the monitoring procedure of the present invention, with its rapid feedback and providing inline, continuous monitoring, this latter assumption has not always been found to be true. Quite contrary to this, it has been found that a reduction in slurry flow does not automatically reduce thickness, moisture content and density but in some cases these variables may be increased, decreased, or remain the same. It is believed that this is because of the interaction between all the variables making up the final product. This cause and effect relationship or actually lack of a cause and effect relationship is important to know because in the past operators have sometimes reduced the slurry flow to the moving screen to decrease thickness, moisture content or density and did not get sufficiently quick feedback to actually determine the effects of these changes. In accordance with the monitoring system of the present invention, the operator will be able to tell almost immediately, at least within 4 minutes whether such a manipulation actually helped or hindered in making the desired change.

What we claim is:

1. A method of monitoring the dry density of a board product made by a wet forming process, which process includes preparing an aqueous slurry of at least some of the compenents making up the product, depositing said slurry on a moving screen to form a moisture-laden sheet thereon, and removing said moisture from said sheet to form said product, said method comprising:
    a. simultaneously and automatically measuring the wet weight, moisture content and thickness of said water-laden sheet while said sheet is on said moving screen; and
    b. from these measurements automatically calculating the dry density of the board product to be produced from the measured sheet.

2. A method according to claim 1 including visually displaying all of said measurements and said dry density.

3. A method according to claim 2 wherein the wet weight, moisture content and thickness of said water-laden sheet are continuously measured during the manufacture of said board product.

4. An assembly for monitoring the dry density of a board product made by a wet forming process, which process includes preparing an aqueous slurry of at least some of the components making up the product, depositing said slurry on a moving screen to form a moisture-laden sheet thereon, and removing said moisture from said sheet to form said product, said assembly comprising:
    a. first means for simultaneously and automatically measuring the wet weight, moisture content and thickness of said water-laden sheet while the said sheet is on said moving screen; and
    b. second means connected to said first means for automatically calculating the dry density of the board product to be produced from the measurements taken on the measured sheet.

5. An assembly according to claim 4 including third means connected to said first means and second means for visually desplaying all of said measurements and said dry density.

6. An assembly according to claim 5 wherein said measuring means continuously measures the wet weight, moisture content and thickness of said water-laden sheet during the manufacture of said board product.

* * * * *